(12) United States Patent
Ripoche et al.

(10) Patent No.: US 10,111,728 B2
(45) Date of Patent: Oct. 30, 2018

(54) PARTIAL SURGICAL GUIDE

(71) Applicant: TROPHY, Rochester, NY (US)

(72) Inventors: Xavier Ripoche, Marne la Vallee (FR); Yann Lecuyer, Paris (FR); Sylvie M. Bothorel, Paris (FR); Helene Goiot, Marne la Vallee (FR); Pascal Narcisse, Marne la Vallee (FR)

(73) Assignee: Trophy, Marne la Vallee (FR)

( * ) Notice: Subject to any disclaimer, the term of this patent is extended or adjusted under 35 U.S.C. 154(b) by 0 days.

(21) Appl. No.: 14/765,350

(22) PCT Filed: Mar. 8, 2013

(86) PCT No.: PCT/EP2013/000688
§ 371 (c)(1),
(2) Date: Aug. 3, 2015

(87) PCT Pub. No.: WO2014/135178
PCT Pub. Date: Sep. 12, 2014

(65) Prior Publication Data
US 2016/0000522 A1    Jan. 7, 2016

(51) Int. Cl.
*A61C 1/08* (2006.01)
*A61B 6/14* (2006.01)
(Continued)

(52) U.S. Cl.
CPC ............. *A61C 1/084* (2013.01); *A61B 6/14* (2013.01); *A61C 8/0089* (2013.01); *A61C 9/0006* (2013.01); *A61C 13/0006* (2013.01)

(58) Field of Classification Search
CPC ....... A61C 1/084; A61C 8/0089; A61C 9/006; A61C 13/0006; A61C 13/0004; A61C 13/0022; A61B 6/14
See application file for complete search history.

(56) References Cited

U.S. PATENT DOCUMENTS 5,575,656 A * 11/1996 Hajjar .................. A61C 5/08
                                            433/165
6,319,000 B1    11/2001 Branemark
(Continued)

FOREIGN PATENT DOCUMENTS

EP    1486900 A1 * 12/2004    ............. A61C 1/084
EP    2 425 796 A1    3/2012
(Continued)

OTHER PUBLICATIONS

International Search Report, International application No. PCT/EP2013/000688, dated Nov. 6, 2013, 2 pages.
(Continued)

*Primary Examiner* — Nicholas Lucchesi
*Assistant Examiner* — Shannel Wright

(57) ABSTRACT

A method for forming a surgical guide for a dental patient rotates material about a rotation axis to a first angular position and drills a drill guiding hole using a drilling tool having a drilling tool axis. The drill guiding hole is centered about a guide axis that is orthogonal to the rotation axis. A first planar surface of the guide is formed from the material, wherein the first surface is. oblique to the guide axis. The material is repositioned to orient the first surface orthogonal to the drilling tool. A hole pattern is formed having two or more positioning holes in the first surface, with the pattern corresponding to a pin pattern in a tray that is positionally registered to a dental arch of the patient. A second planar surface of the surgical guide is formed, parallel to the first planar surface.

11 Claims, 17 Drawing Sheets

(51) Int. Cl.
*A61C 8/00* (2006.01)
*A61C 9/00* (2006.01)
*A61C 13/00* (2006.01)

(56) References Cited

U.S. PATENT DOCUMENTS

| | | | | |
|---|---|---|---|---|
| 6,319,006 | B1* | 11/2001 | Scherer | A61C 1/084 433/215 |
| 6,814,575 | B2* | 11/2004 | Poirier | A61C 1/084 433/75 |
| 7,086,860 | B2* | 8/2006 | Schuman | A61C 1/084 433/75 |
| 7,097,451 | B2* | 8/2006 | Tang | A61B 17/176 433/76 |
| 7,731,497 | B2* | 6/2010 | De Moyer | A61C 1/084 433/72 |
| 8,135,492 | B2* | 3/2012 | Yau | A61C 1/084 264/101 |
| 8,167,615 | B2* | 5/2012 | Jacotti | A61C 1/084 433/75 |
| 8,794,964 | B2* | 8/2014 | Haber | A61C 1/084 433/75 |
| 8,892,235 | B2* | 11/2014 | Choi | A61C 1/084 433/201.1 |
| 9,011,148 | B2* | 4/2015 | Dolfi | A61C 1/084 433/213 |
| 2005/0112524 | A1* | 5/2005 | De Clerck | A61C 1/084 433/76 |
| 2006/0003292 | A1* | 1/2006 | Lauren | A61C 5/007 433/215 |
| 2007/0154862 | A1* | 7/2007 | Kim | A61C 1/084 433/72 |
| 2008/0166681 | A1* | 7/2008 | Weinstein | A61C 1/084 433/76 |
| 2008/0176187 | A1* | 7/2008 | Stumpel | A61C 1/084 433/196 |
| 2009/0136902 | A1* | 5/2009 | Zundorf | A61C 8/0089 433/223 |
| 2009/0274990 | A1* | 11/2009 | Kim | A61B 17/176 433/75 |
| 2010/0028826 | A1* | 2/2010 | Jacotti | A61C 1/084 433/72 |
| 2012/0053593 | A1* | 3/2012 | Abboud | A61C 1/084 606/96 |
| 2012/0177456 | A1* | 7/2012 | Jung | B23C 3/00 408/1 R |
| 2012/0225409 | A1* | 9/2012 | Baumann | A61C 1/084 433/214 |
| 2013/0071811 | A1* | 3/2013 | Groscurth | A61C 1/084 433/75 |
| 2013/0144417 | A1* | 6/2013 | Pieper | A61C 1/084 700/98 |
| 2014/0162213 | A1* | 6/2014 | Haber | A61C 13/0019 433/173 |
| 2014/0186796 | A1* | 7/2014 | Suttin | A61C 8/0001 433/172 |
| 2015/0045803 | A1* | 2/2015 | Deville | A61C 1/084 606/96 |

FOREIGN PATENT DOCUMENTS

| | | | | |
|---|---|---|---|---|
| EP | 2425796 A1 * | 3/2012 | | A61C 1/084 |
| FR | 2 825 614 | 6/2001 | | |
| WO | 2005/055852 A2 | 6/2005 | | |
| WO | WO 2005055852 A2 * | 6/2005 | | A61B 17/176 |

OTHER PUBLICATIONS

Guillaume et al., Kohler Medizintechnik, Clinical Report, Wintray, pp. 1-12, 2007.
Van Steenberghe et al., A Computed Tomographic Scan-Derived Customized Surgical Template and Fixed Prosthesis for Flapless Surgery and Immediate Loading of Implants in Fully Edentulous Maxillae: A Prospective Multicenter Study, Clinical Implant Dentistry and Related Research, vol. 7, Supplemental 1, pp. S111-S120, 2005.
Sirona, Excursion meets Galileos, Implant Precision, pp. 1-17, Feb. 2010.

* cited by examiner

PARTIAL SURGICAL GUIDE

CROSS REFERENCE TO RELATED APPLICATIONS

This application claims the benefit of and is a U.S. National Phase filing of PCT Application PCT/EP2013/000688 filed Mar. 8, 2013 entitled "PARTIAL SURGICAL GUIDE", in the name of Ripoche et al. which is incorporated herein by reference in its entirety.

FIELD OF THE INVENTION

The invention relates generally to the field of surgical implant positioning, and more particularly to a surgical guide for drilling in order to position an implant within the jaw bone.

BACKGROUND OF THE INVENTION

Dental implants are used to replace missing or badly damaged teeth. In order to mount a dental implant securely in bony tissue, a hole must be drilled into supporting bone structure, such as into the mandibular or maxillary jaw bone of the patient. The implant portion that holds the artificial tooth is usually made of titanium or a titanium alloy and must be able to rapidly integrate with the bone of the patient. Once the implant is properly seated and secure, the artificial tooth can be installed.

Osteotomy and related procedures in which a hole is drilled into the maxillary or mandibular jaw bone at the proper angle and dimension, requires a good degree of accuracy, so that the implant fits correctly without damage to surrounding tissue or structures and so that the completed work is aesthetically acceptable. For edentulous or at least partially edentulous patients, implant planning is carefully executed. Based on information from x-ray or computerized tomography (CT) imaging of the patient's dental arch, dedicated software tools allow the dentist to define the location, diameter, length or drill depth, shape and angulation of the implant to be affixed on the patient's jaw bone. One consideration in this planning is reducing the risk of damage to nearby nerves or blood vessels.

One appliance that is used to assist in implant preparation is the surgical guide. Custom-fabricated for each patient, shaped to conform to at least a portion of the patient's dental arch, the surgical guide must be fitted to the patient's mouth and should include one or more guide holes to guide the dental drill into the supporting bone according to the implant planning.

The surgical guide used for this purpose can be fabricated as a plastic appliance using a stereolithographic process or by a milling process, based on the digital data obtained during implant planning. Some dental sites are equipped with a 4-axis milling machine for dental prostheses, enabling the surgical guide to be prepared on-site. Though 5-axis milling equipment is available, the 4-axis milling machine is capable for use with other dental prostheses including for milling a surgical guide. There are limitations to 4-axis devices for forming surgical guides having suitable characteristics for some types of procedure.

In addition to providing the capability for straightforward fabrication, there are a number of other challenges for designing a surgical guide that facilitates osteotomy and related drilling procedures. Size is one consideration; the guide should be sizable enough to provide stability for the rotating drill, but should not be uncomfortable for the patient. The guide should be formed from a suitably durable, non-toxic material. The design for a surgical guide should register readily in the mouth of the patient, so that the drill location and angle are precisely controlled and can be customized for the particular patient.

Thus there is need for a surgical guide that is easy to use, that can be readily fabricated using less expensive equipment and customized for an individual patient, that can be designed for use with specialized software for implant planning, and that has reduced cost over more complex drill guide alternatives.

SUMMARY OF THE INVENTION

Embodiments of the present invention advance the art of implant preparation and installation by providing a surgical guide for drilling procedures for drilling into supporting bone. Advantageously, embodiments of the present invention allow fabrication of a surgical guide for drilling using a 4-axis milling apparatus. Methods of the present invention help to overcome inherent limitations of 4-axis milling for forming a surgical guide that can be readily used for a range of procedures.

According to one aspect of the invention, there is provided a method for forming a surgical guide for drilling of a dental patient, the method comprising: rotating a block/shape/piece of material about a rotation axis to a first angular position; drilling a drill guiding hole through the material using a drilling tool having a drilling tool axis, wherein the drill guiding hole is centered about a guide axis that is substantially orthogonal to the rotation axis; forming a first planar surface of the surgical guide from the block of material, wherein the first surface is oblique to the guide axis; repositioning the block of material to orient the first surface orthogonal to the drilling tool; forming a hole pattern having two or more positioning holes in the first surface, wherein the hole pattern corresponds to a pin pattern in a tray that is positionally registered to a dental arch of the patient; and
forming a second planar surface of the surgical guide, wherein the second planar surface is parallel to the first planar surface.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
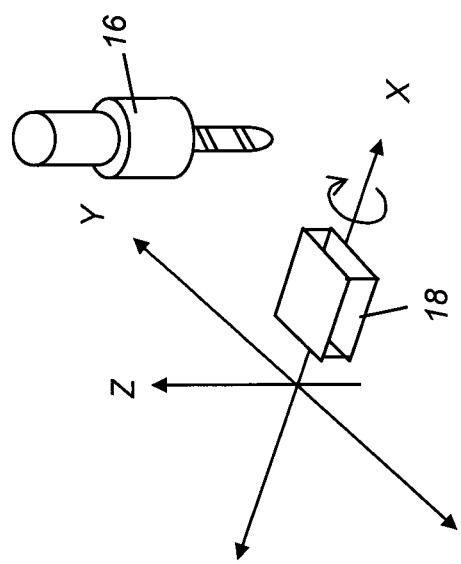
FIG. 1 shows coordinate designations used in the context of the present disclosure.

The following is a detailed description of preferred embodiments of the invention, reference being made to the drawings in which the same reference numerals identify the same elements of structure in each of the several figures. Similar descriptions concerning components and arrangement or interaction of components already described are omitted. Where they are used, the terms "first", "second", and so on, do not necessarily denote any ordinal or priority relation, but are simply used to more clearly distinguish one element from another.

In the context of the present disclosure, two features, such as lines or surfaces, are considered to be substantially orthogonal or perpendicular if the angle between them differs by less than about 3 degrees from an odd integer multiple of 90 degrees (for example, 90 degrees or 270 degrees). Two features are considered to be parallel, or substantially parallel, if the angle between them differs by less than about 3 degrees from an integer multiple of 180 degrees (for example, 0 degrees or 180 degrees).

In the context of the present disclosure, the term "oblique" describes an angular relationship wherein two lines or surfaces, or a line and a surface, are not parallel and not orthogonal, and wherein the angle between them is offset by at least more than about 3 degrees from any integer multiple of 90 degrees.

In the context of the present disclosure, terms such as "top" and "bottom" or "above" and "below" or "beneath" or "up" and "down" are relative and do not indicate any necessary orientation of a component or surface, but are used simply to refer to and distinguish views, opposite surfaces, or spatial relationships. Similarly, terms "horizontal" and "vertical" may be used relative to the figures, to describe the relative orthogonal relationship of components in different planes, for example, but do not indicate any required orientation of components with respect to true horizontal and vertical orientation.

Where they are used, the terms "first", "second", "third", and so on, do not necessarily denote any ordinal or priority relation, but are used for more clearly distinguishing one element or time interval from another. These descriptors are used to clearly distinguish one element from another similar element in the context of the present disclosure.

A 4-axis milling machine used in a conventional manner is somewhat limited in function for forming a surgical guide and, using conventional practices, is unsuited for providing guidance holes at some angles. Referring to FIG. 1, there are shown coordinate designations for 4-axis machining. The 4-axis milling apparatus can translate a workpiece 18 with respect to a tool 16 along each of the axes X, Y, and Z, and can rotate the workpiece about the X-axis. This allows the 4-axis milling machine to drill holes tilted in the YZ plane; however, a 4-axis milling apparatus is not designed to drill holes that are tilted in other planes. A surgical guide, however, often requires drilling for guide holes at angles other than those in the YZ plane. Thus, there is a need for methods and apparatus that allow 4-axis milling equipment to be used for machining surgical guides having guide holes at various angles.

Figure 2:
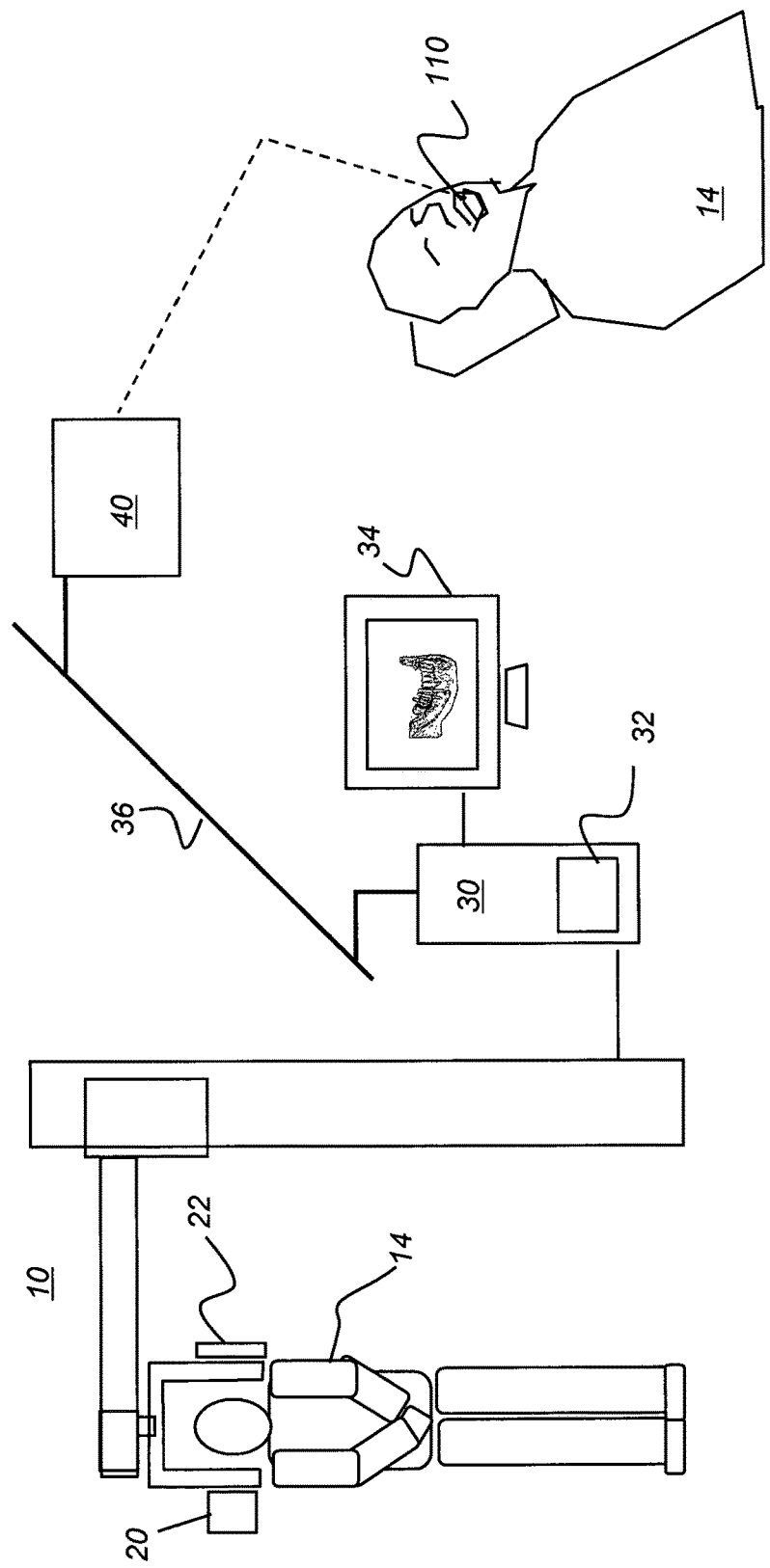
FIG. 2 is a block diagram that shows an imaging system for implant planning.

Embodiments of the present invention address the problem of fabricating a surgical guide on a 4-axis milling machine by using a disposable arch registration tray that is configurable to the mouth of an individual patient and has mounting features that allow accurate and repeatable positioning of a machined surgical guide. In order to better understand the role of the surgical guide and its relationship to imaging and implant planning utilities, it is useful to consider how a system for implant management is arranged. Referring to FIG. 2, there is shown a dental system for implant planning. An imaging apparatus 10, such as a cone-beam computed tomography (CBCT) or other 3-dimensional (3-D) imaging apparatus, obtains image content for one or more dental arches of a patient 14 by orbiting a radiation source 20 and imaging detector 22 about the head of patient 14. Once a 3-D image of the oral volume of the patient has been reconstructed on the basis of the scan data, the image data is used by a computer apparatus 30 that executes instructions from implant planning software 32. The resulting image and implant information displays on a display 34 that is in signal communication with computer 30. The implant information generated by planning software 32 is also used to generate fabrication data that goes to a milling apparatus 40, such as a 4-axis milling apparatus. Milling apparatus 40 may connect to computer 30 over a network 36. Milling apparatus 40 is then used to fabricate a partial surgical guide 110 that is used for drilling in implant preparation and placement.

Figure 3:
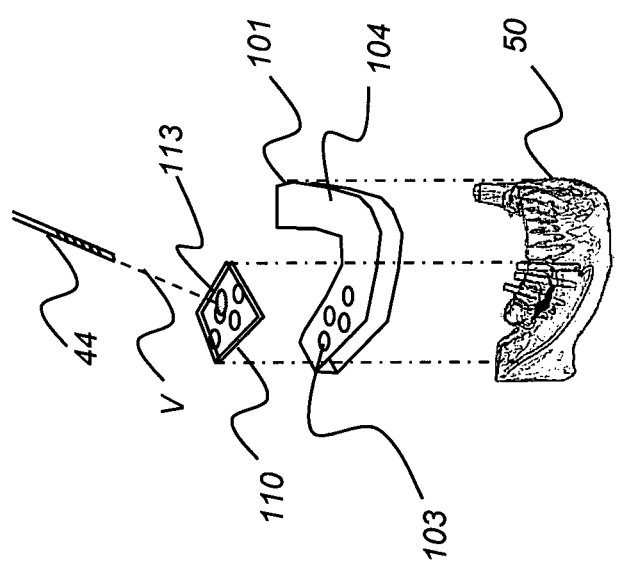
FIG. 3 is a perspective view that shows how a partial surgical guide relates to the dental arch.

FIG. 3 is an exploded view that shows how partial surgical guide 110 relates to a dental arch 50. A plastic registration tray 101 is prepared and registered to arch 50, as described in more detail subsequently. Surgical guide 110 fits onto plastic tray 101 in a fixed position, using a pattern of pins 103 formed on a surface 104 and includes a guiding hole 113 for guiding the dentist's drill 44 along a guide axis V.

Figure 4:
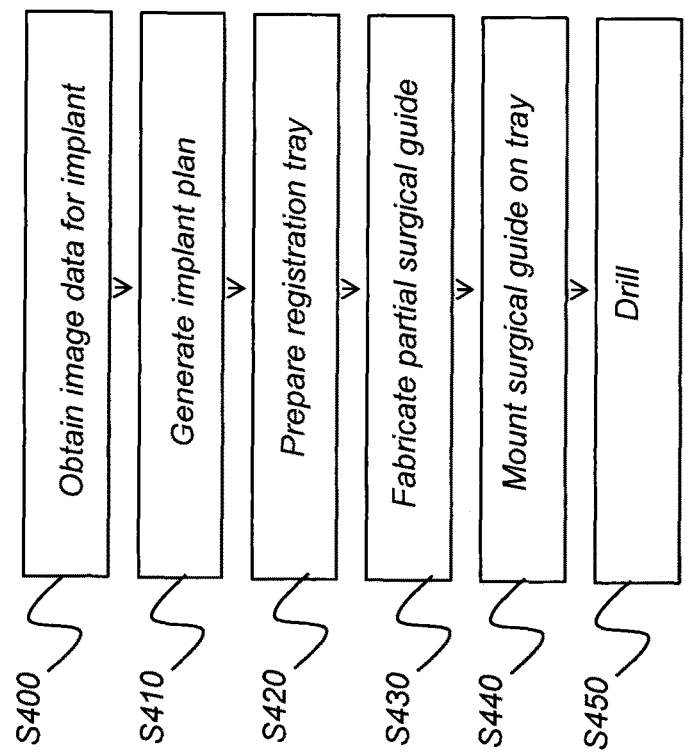
FIG. 4 is a logic flow diagram showing the sequence for forming and using the surgical guide according to an embodiment of the present invention.

Steps for implant preparation using the surgical guide according to an embodiment of the present invention are shown in FIG. 4 and include the following:

Step S400: Obtain image data for the implant. As described previously, the image data can be volume image data obtained from a CBCT or other 3-D imaging system.

Step S410: Generate an implant plan according to the image data, such as using implant planning software. Implant planning software products are well known to those in the dental arts. This software generates information or recommendations on drill location, angle, and depth dimensions, for example.

Step S420: Prepare the registration tray. Plastic tray 101 (FIG. 3) is filled with an impression forming material, such as alginate or silicon for example. The tray is placed over the dental arch and the patient bites down to form an impression that registers the tray 101 to the same position within the patient's mouth. The tray is removed when the impression forming material has set.

Step S430: Fabricate the partial surgical guide 110. Fabrication steps are described in more detail subsequently.

Step S440: Mount the fabricated partial surgical guide 110 on tray 101 and position the guide in the patient's mouth.

Step S450: Drill the hole for the implant according to the guiding hole in partial surgical guide 110.

The tray and its mounted surgical guide 110 can then be removed from the patient's mouth.

Figure 5:
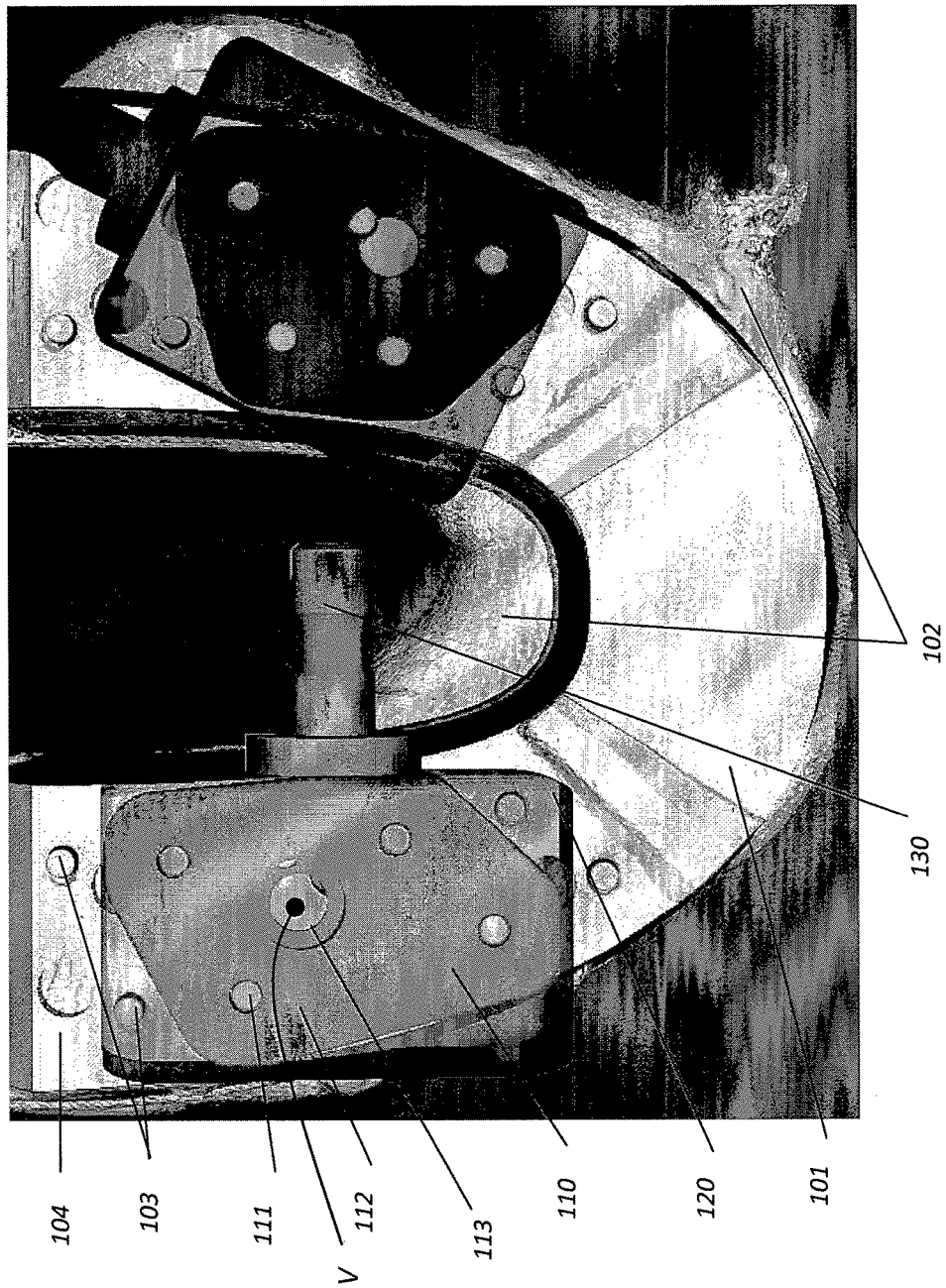
FIG. 5 is a plan view that shows a plan for surgical guide fabrication according to an embodiment of the present invention.

FIG. 5 shows aspects of the design and placement of partial surgical guide 110, as viewed on the computer display 34 (FIG. 2) using implant planning software, according to an embodiment of the present invention. Plastic registration tray 101 is shown filled with impression forming material 102. In a sequence familiar to those who obtain dental impressions, as described with reference to step S420 in FIG. 4, tray 101 has been positioned over the teeth. The impression is formed when the patient bites into impression forming material 102. Once the impression forming material 102 has hardened, tray 101 is removed from the patient's mouth. As the material 102 contains the teeth print of the patient, tray 101 can be repositioned in the patient's mouth in very repeatable positioning conditions and can then be used as a guide for the surgical drilling process.

Tray 101 includes one or more alignment features in the form of a pattern of small raised pins 103 that protrude from the surface 104 of tray 101. Guide 110 has a corresponding set of positioning holes 111 in a pattern that matches the pattern of pins 103, so that holes 111 cooperate with pins 103 to align guide 110 to tray 101. Holes 111 are perpendicular to an upper planar surface 112 of the guide 110 and can extend partially or completely through the body of guide 110. With pins 103 seated within holes 111, the position of surgical guide 110 is well-defined and its spatial registration within the patient's mouth is repeatable.

A guiding hole 113 defines a guide axis V (shown more clearly in FIG. 3) to guide the dentist's drilling tool when drilling the holes in the patient's jaw bone. Guiding hole 113 is defined according to the virtual implant planning.

Typically, guiding hole 113 is tilted/angled so that it is oblique relative to the planar surfaces of the partial guide 110 and is also oblique relative to positioning holes 111.

Fabrication

A standard-sized, molded or otherwise pre-formed tray 101 can be used for the majority of patients, such as having one size for adult patients, for example. However, surgical guide 110 is customized for each patient, with its guiding hole 113 provided at the proper location and angle for each individual implant site. Embodiments of the present invention provide a design that is well-suited to the constraints of a 4-axis milling apparatus, allowing a range of drill angles and locations to be obtained by following a standard procedure.

Figure 6:
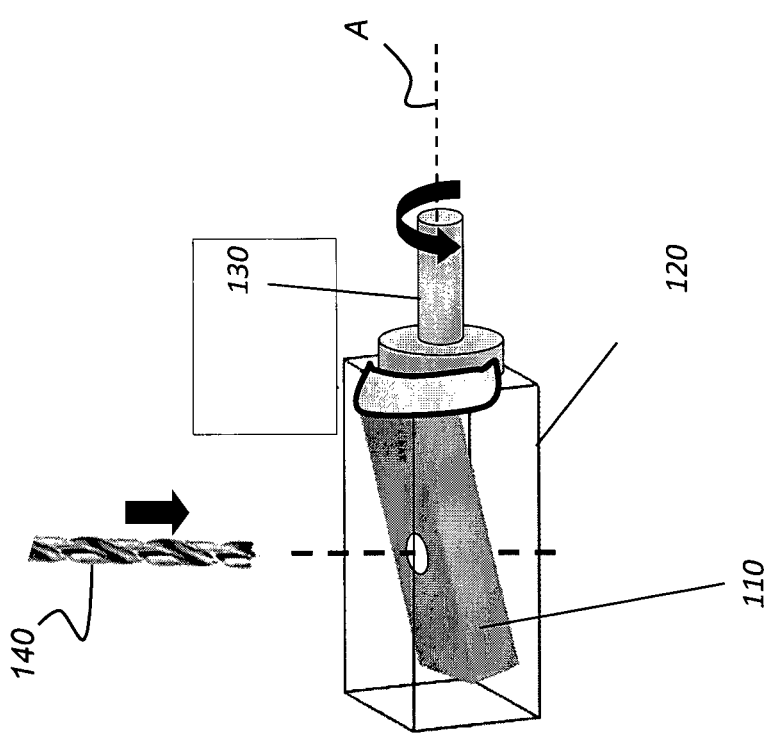
FIG. 6 is a perspective view that shows how the surgical guide is formed from a block/shape of material.

In FIG. 6, the virtual partial surgical guide 110 is represented in partial transparency within a virtual raw block/shape/supply/piece of material 120. As illustrated, significant portions of block 120 are removed by machining in order to form surgical guide 110. The perspective view of FIG. 6 shows a standard block 120 having a block holder 130 for fixing to the mandrel of a milling apparatus, such as apparatus 40 (FIG. 2). An axis A of mandrel rotation is shown.

Figure 7:
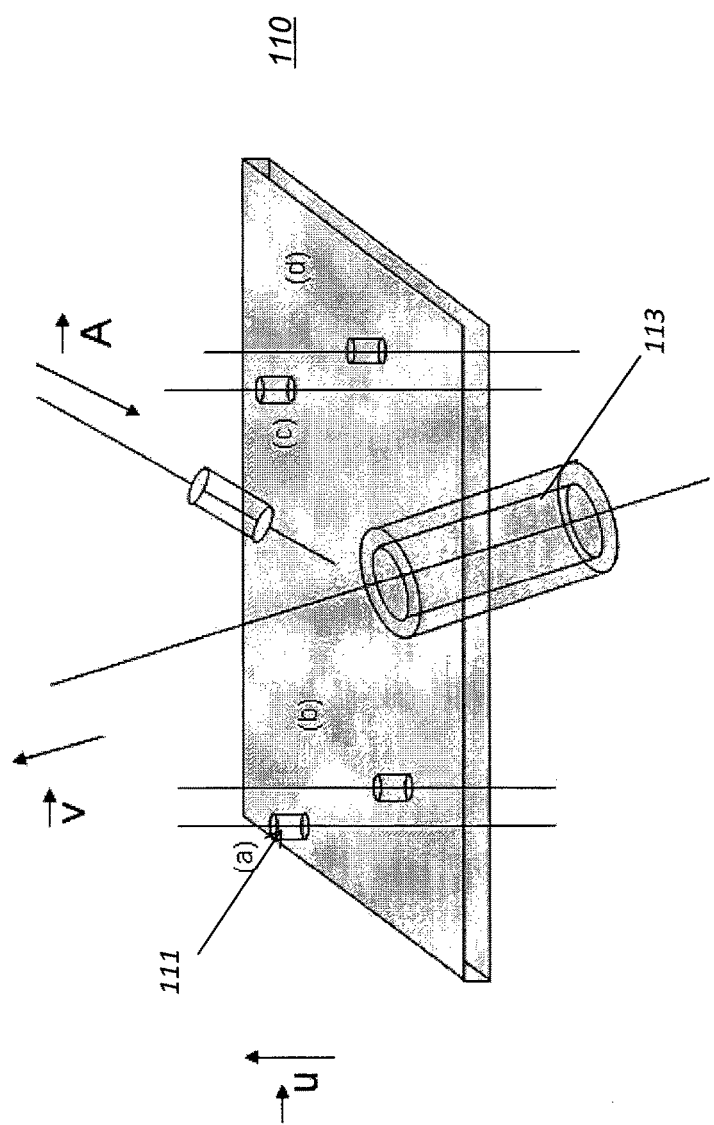
FIG. 7 is a perspective view that shows the orientation of different axes for surgical guide rotation and fabrication.
Figure 8:
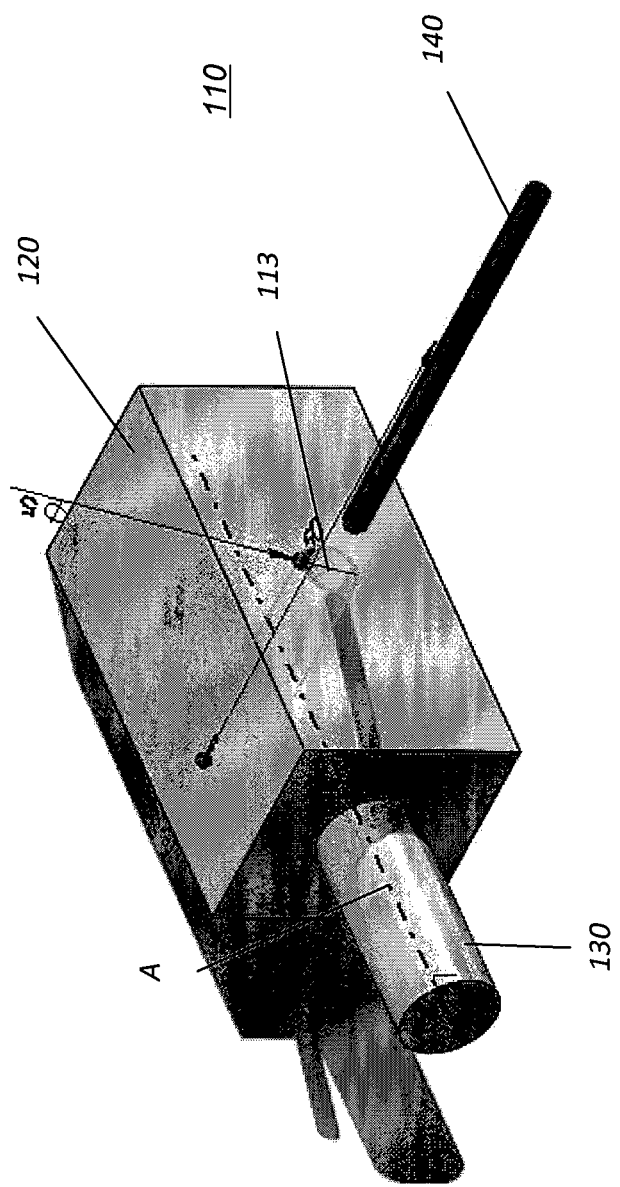
FIG. 8 is a perspective diagram that shows drilling a guiding hole.
Figure 9:
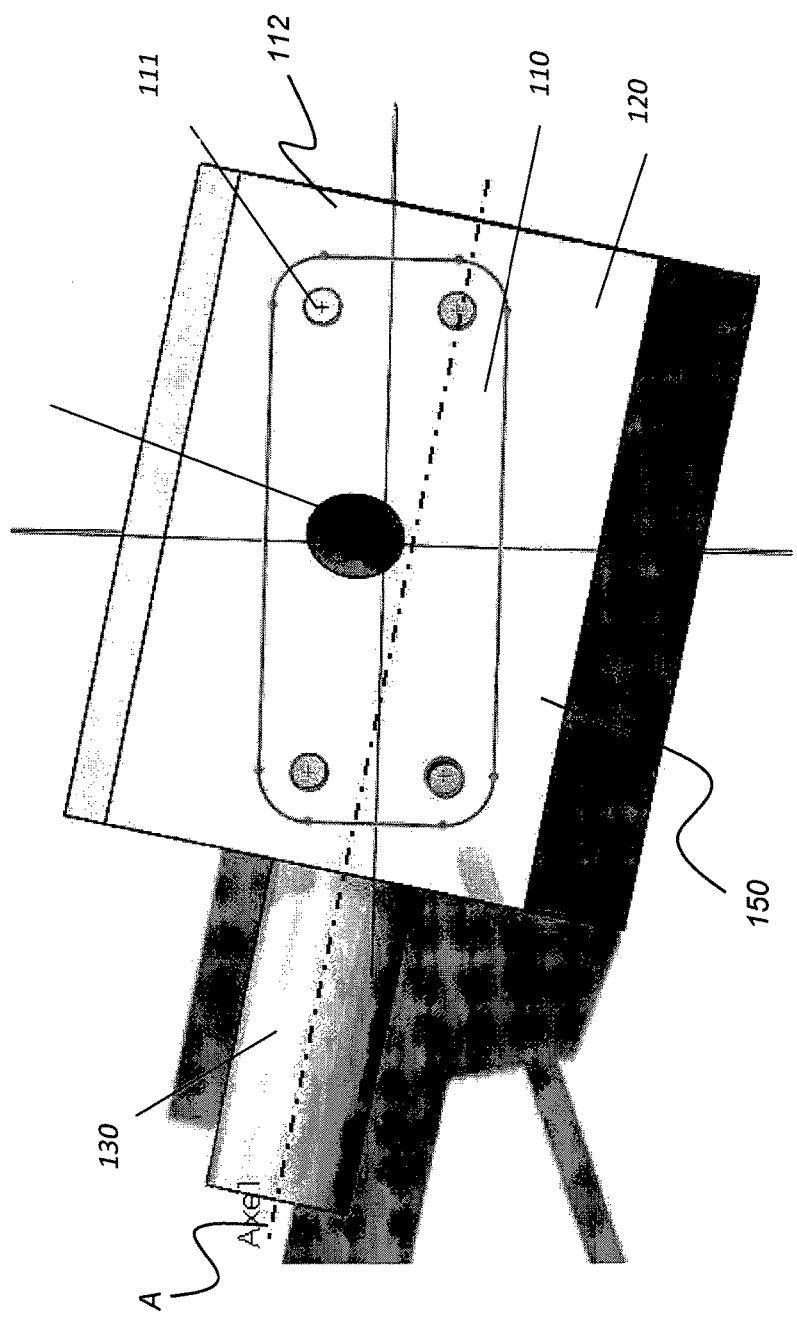
FIG. 9 is a plan view that shows the guiding and positioning holes relative to a machined surface of the surgical guide.
Figure 10:
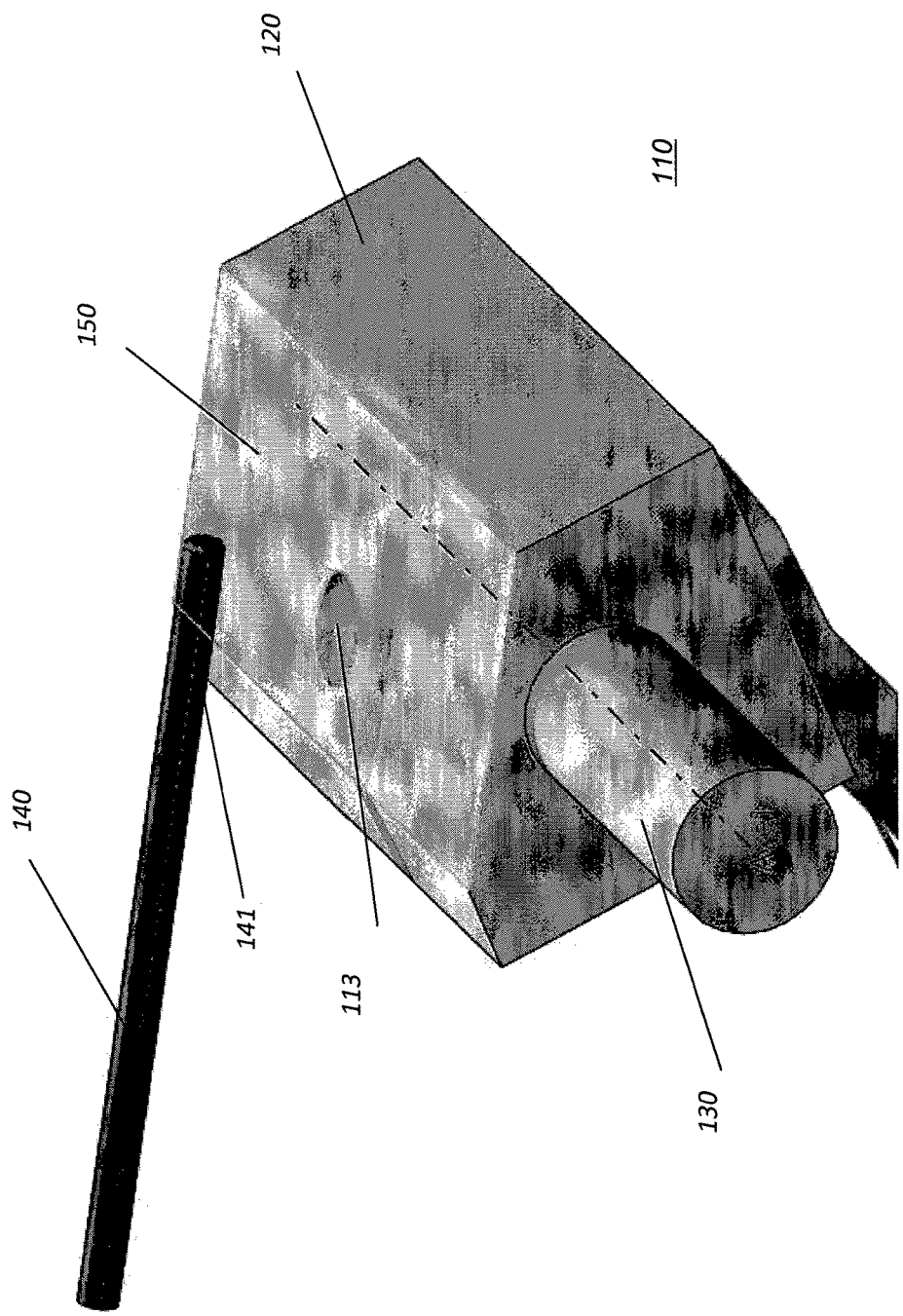
FIG. 10 is a perspective view showing the block with one milled surface in an intermediate fabrication stage.

For fabrication, block holder 130 can rotate relative to the milling machine and to a drilling tool 140 of the milling apparatus that moves along the direction of the arrow of FIG. 6. As this figure indicates, the machine drills holes only in a plane that is orthogonal to axis A of block holder 130. As shown with respect to FIGS. 7, 8, and 9, in order to be able to drill the positioning holes 111 and guiding hole 113, it is necessary to rotate the virtual partial surgical guide 110 about an axis parallel to the direction of the axes of the positioning holes 111 so that both the guide axis V of the tilted guiding hole 113 and the axes U of the positioning holes 111 lie in planes orthogonal to the axis A during the drilling operation. Then, as represented in FIG. 7, the axes U of the positioning holes 111 and the guide axis V of the guiding holes 113 are located in planes orthogonal to axis A of the block holder. FIG. 10 shows a portion of block 120 removed to provide a tilted planar surface 150 that forms surface 112 of guide 110.

Figure 11:
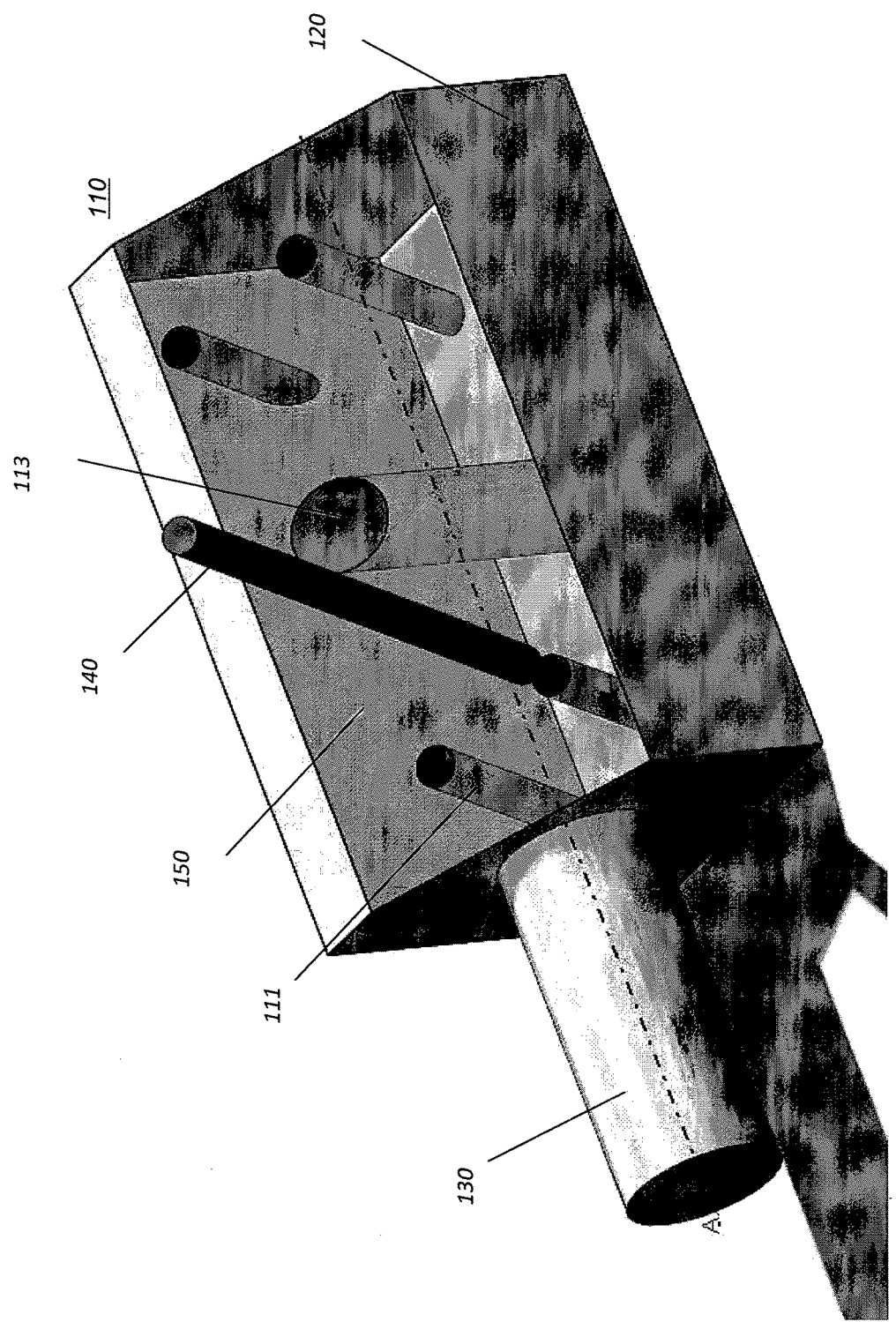
FIG. 11 is a perspective view that shows drilling one of the positioning holes.

According to a fabrication sequence in an embodiment of the present invention, as shown in FIGS. 8 through 11, guiding hole 113 is first drilled orthogonally to the surface of block 120. Then, block 120 is rotated relative to drilling tool 140 so that a tilted surface 150 is milled, machined by the lateral surface 141 of the drilling tool (FIG. 10). The tilt of the machined surface 150 relative to the guiding hole 113 is determined so that the axis of the positioning holes 111 to be drilled are orthogonal to the tilted surface 150, as shown in FIG. 11. The block is rotated again so that the tool 140 can drill the positioning holes 111 orthogonally to the tilted surface 150.

Figure 12:
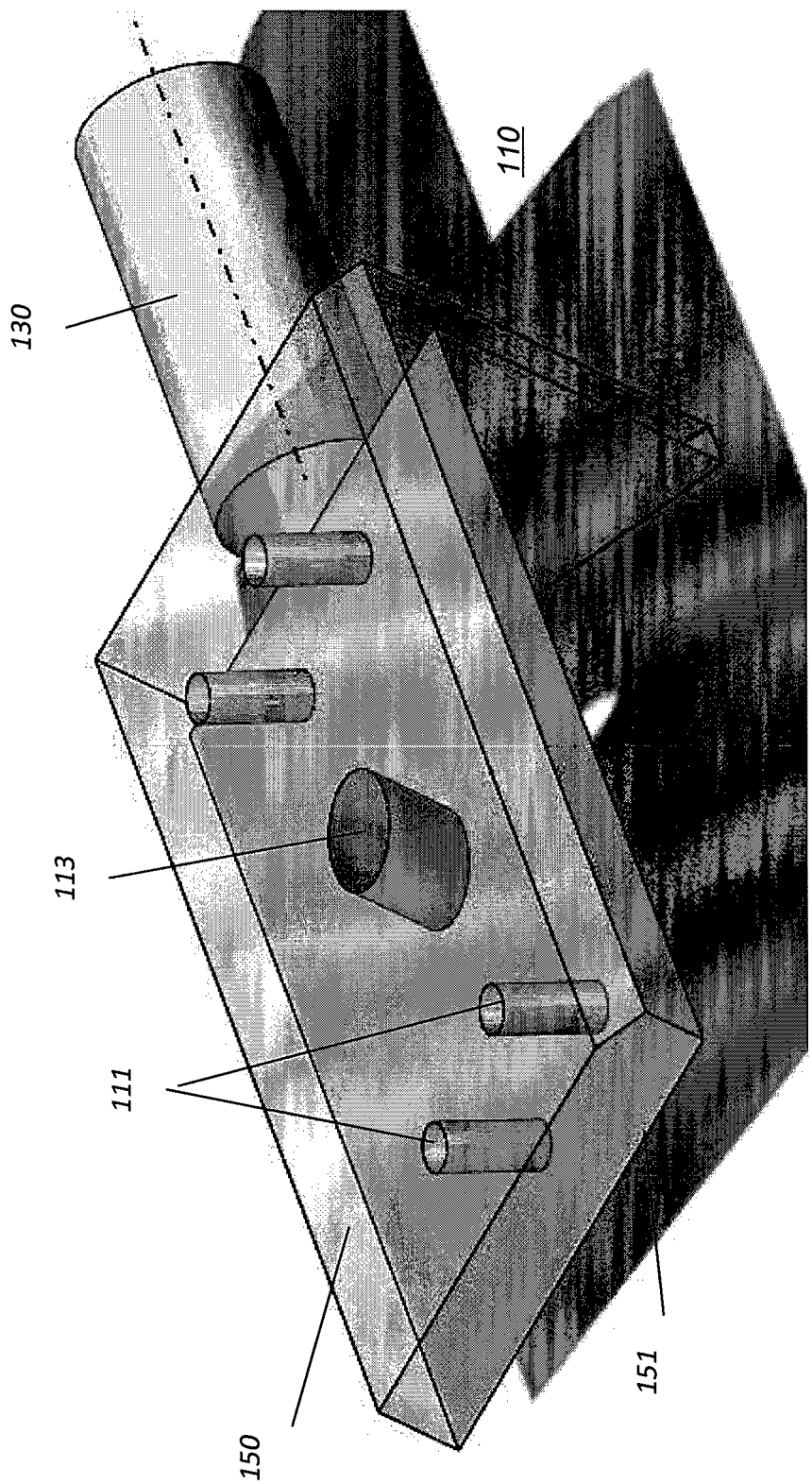
FIG. 12 is a perspective view showing top and bottom surfaces milled from the block.

FIG. 12 shows a subsequent fabrication step in which a second surface 151 opposite and parallel to the first surface 150 is milled by the lateral surface of the tool. Once partial surgical guide 110 has been milled, the last portion of material linking partial surgical guide 110 to block handle 130 is cut. Before positioning partial surgical guide 110 on plastic tray 101, the area of the tray where drilling guide hole 113 will be positioned is removed. A rough hole is then formed through the ensemble comprising plastic tray 101 and the hardened setting material 102 inside the tray so that partial surgical guide 110 can be installed. The partial surgical guide 110 can then be positioned on tray 101. Pins 103 of tray 101 penetrate positioning holes 111 of partial surgical guide 110 for a fixed spatial relationship between the tray and the partial surgical guide. The ensemble comprising tray 101 and partial surgical guide 110 can be positioned in the patient's mouth. As noted above, the ensemble is in a fixed and well defined registration with the patient's dentition because the print of the patient's teeth on the hardened silicone material inside the plastic tray fits precisely on the patient's dentition. The surgery then consists in drilling holes in the patient's jaw bone by inserting the drilling tool inside the guiding hole 113.

Surgical guide 110 can be formed from metal, ceramic, or other suitable material, including some types of plastics, such as PMMA (Poly(methyl methacrylate)) plastic, for example. Other machinable materials can also be employed for forming surgical guide 110.

Figure 13A:
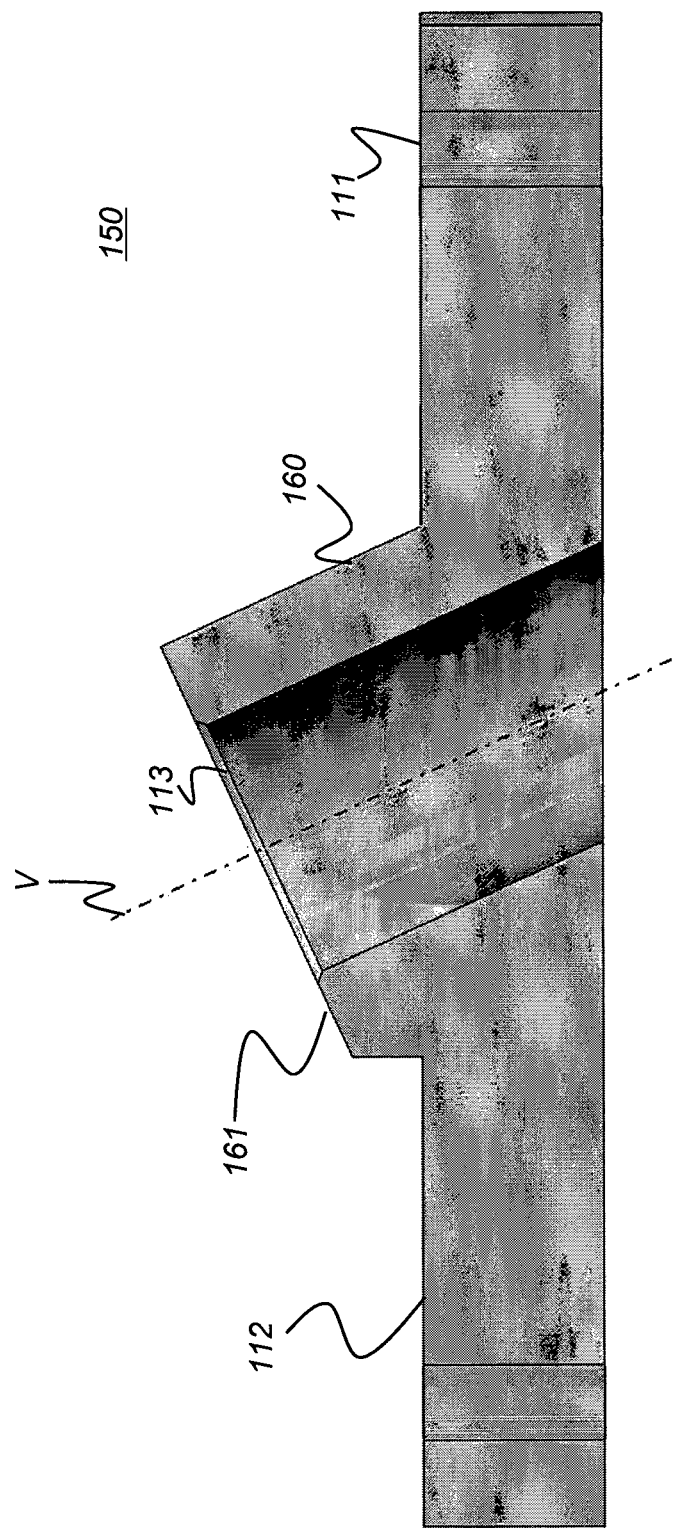
FIG. 13A is a cross-sectional view of a surgical guide according to an alternate embodiment of the present invention.
Figure 13B:
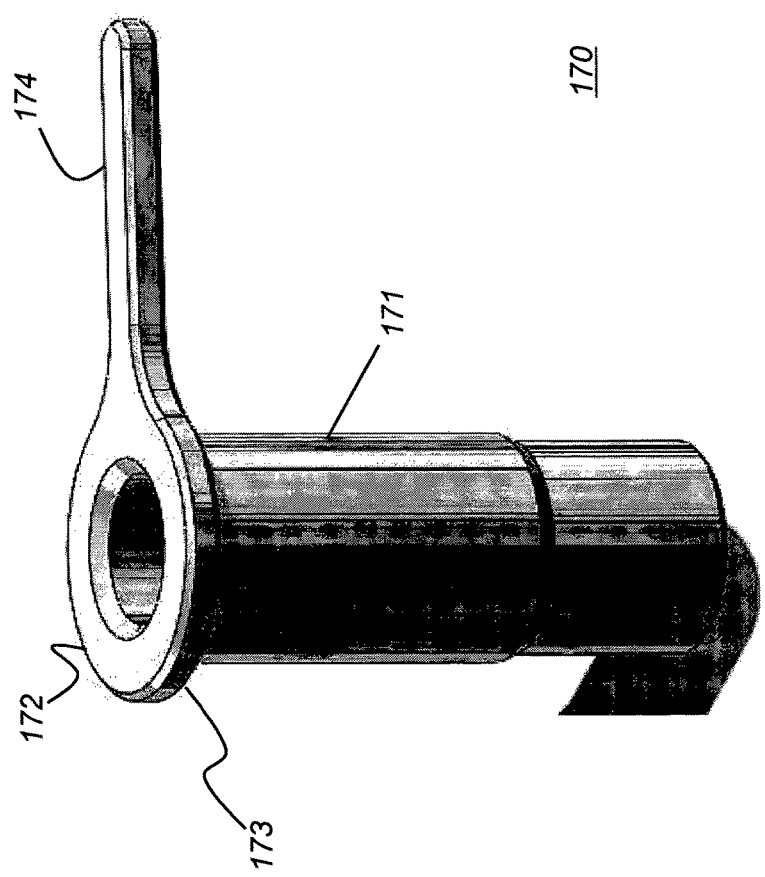
FIG. 13B is a perspective view showing a drilling guide insert that can be used with the surgical guide of FIG. 13A.
Figure 13C:
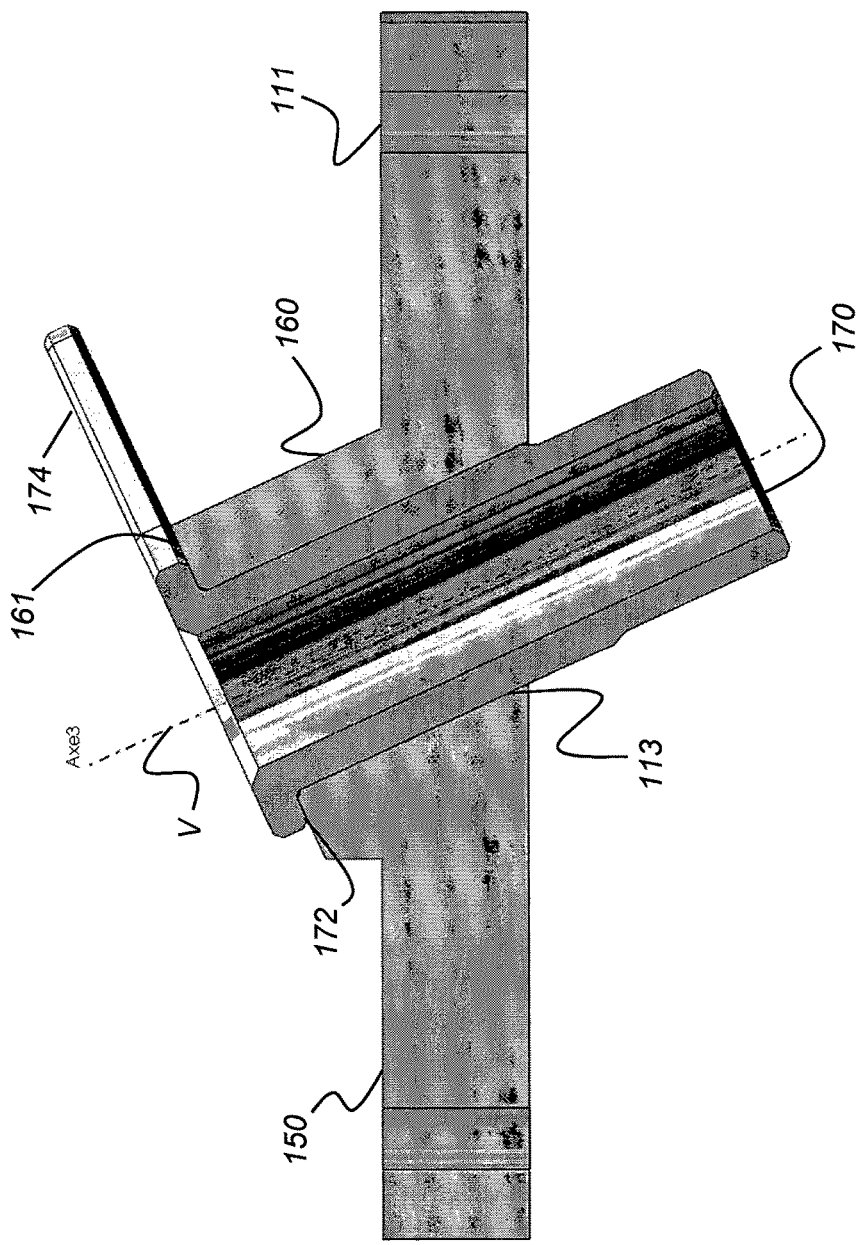
FIG. 13C is a cross-sectional view showing the drilling guide insert of FIG. 13B seated within the drill guiding hole of the surgical guide of FIG. 13A.

FIGS. 13A, 13B, and 13C show an alternate embodiment of a surgical guide 150 that has similar fabrication to that described for surgical guide 110, with added features for improved usability and accuracy in some cases. FIG. 13A is a cross-sectional view of surgical guide 150 according to an alternate embodiment of the present invention. During the milling operation, a shoulder 160 is provided having a face 161 that is orthogonal to guide axis V for guiding hole 113; face 161 is oblique to surface 112. Guiding hole 113 is sized for an insert, as shown in the perspective view of FIG. 13B. FIG. 13B shows a drilling guide insert 170 that can be used with the surgical guide 150 of FIG. 13A. Typically formed from metal or other machined material, drilling guide insert 170 has a sleeve 171 having an outer diameter that is slightly less than the inner diameter of guiding hole 113 (FIG. 13A). A shoulder 172 has a lower rim 173 for accurate seating of insert 170 within the surgical guide 150, as described subsequently. A handle 174 allows more convenient handling, placement, and manipulation of insert 170 by the practitioner.

FIG. 13C is a cross-sectional view showing drilling guide insert 170 of FIG. 13B installed within surgical guide 150. Insert 170 fits snugly into guiding hole 113, seated within guiding hole 113 with shoulder 172 abutted against face 161. For drilling, the practitioner inserts a drilling tool through sleeve 171 of insert 170 to drill along axis V.

Figure 14:
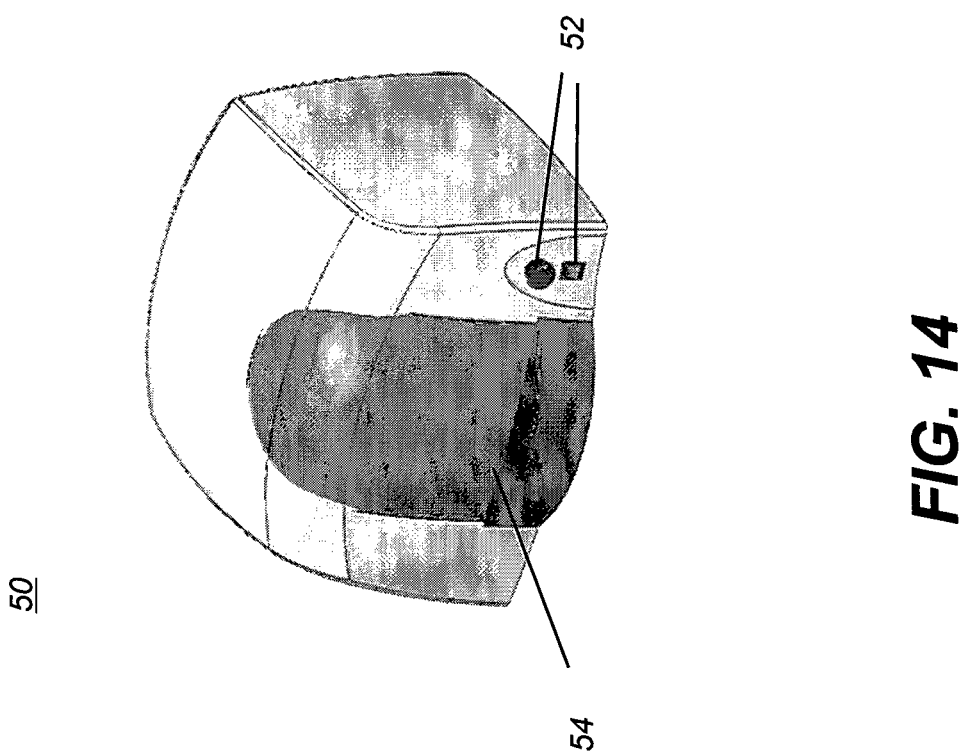
FIG. 14 is a perspective view of a 4-axis milling apparatus that can be used for forming the surgical guide.
Figure 15:
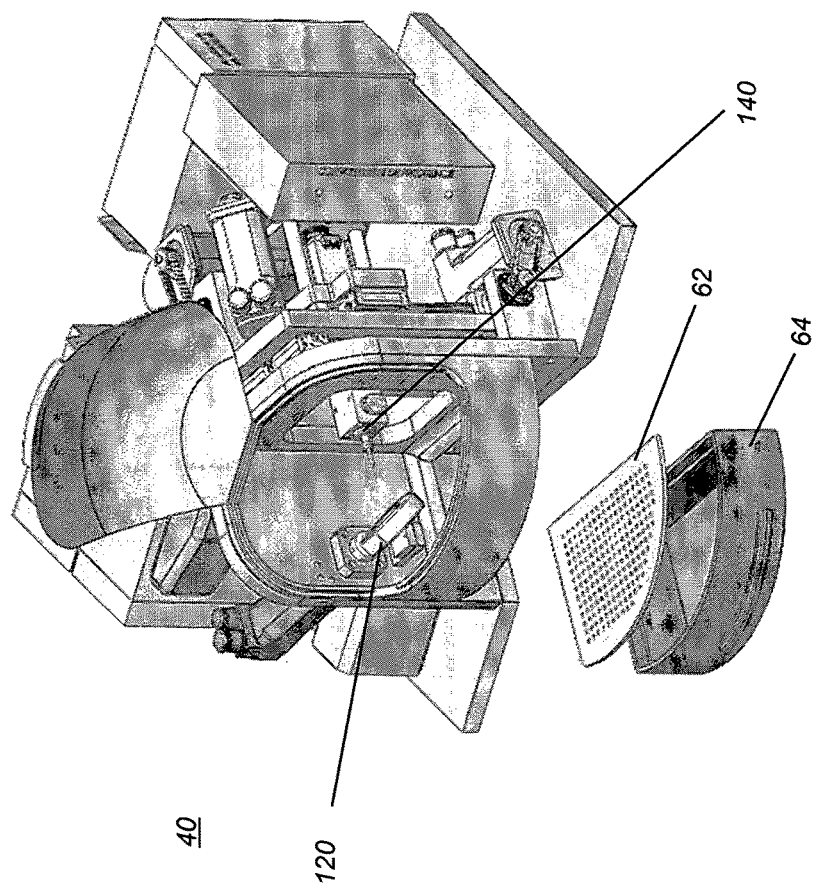
FIG. 15 is a perspective view, in partial exploded view form, of a 4-axis milling apparatus for forming the surgical guide.

FIG. 14 shows a small-scale milling apparatus 40 that can be used for surgical guide fabrication in a dental office or other facility. Milling apparatus 40 obtains data about partial surgical guide 110 from planning software 32 (FIG. 2) and performs the fabrication steps necessary to automatically generate or surgical guide 110. According to an embodiment of the present invention, this data is obtained from processing a volume image of the patient to generate an implant plan that shows the position of a planned implant relative to patient features. Additional information about the surgery type is obtained and used for generating the implant plan. Apparatus 40 has a protective door 54 and controls 52 for initiating operation and reporting process completion or error. The partially exploded view of FIG. 15 shows internal components of milling apparatus 40, including a filter 62 and a water tank 64. The relative positions of a workpiece block 120 and a tool 140 are also shown by way of example.

Consistent with an embodiment of the present invention, a computer program on computer apparatus 30 (FIG. 2) utilizes stored instructions that perform on imaging and fabrication data that is accessed from an electronic memory. As can be appreciated by those skilled in the imaging and computer-aided manufacturing arts, a computer program of an embodiment of the present invention can be utilized by a suitable, general-purpose computer system, such as a personal computer or workstation. However, many other types of computer systems can be used to execute the computer program of the present invention, including an arrangement of networked processors, for example. The computer program for providing fabrication data that supports the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the computer or host processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various data manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the imaging and automated fabrication processing arts. Additional aspects of such algorithms and systems, and hardware and/or software for producing and otherwise processing the imaging or fabrication data or co-operating with the computer program product of the present invention, are not specifically shown or described herein and may be selected from such algorithms, systems, hardware, components and elements known in the art.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:
1. A method for forming a surgical guide for drilling of a dental patient, comprising:
   mounting a block of machinable material having a prescribed shape to a holder;
   rotating the block of machinable material by the holder about a rotation axis to a first angular position;
   drilling a drill guiding hole through the block of machinable material using a drilling tool having a drilling tool axis that is orthogonal to the rotation axis, wherein the drill guiding hole is centered about a guide axis that is substantially orthogonal to the rotation axis;
   repositioning the block of machinable material by the holder and forming a first planar surface of the surgical guide from the block of machinable material using the drilling tool, wherein the first planar surface is oblique to the guide axis;

repositioning the block of machinable material to orient the first planar surface orthogonal to the drilling tool axis;

forming a hole pattern having two or more positioning holes in the first planar surface using the drilling tool, wherein the hole pattern corresponds to a pin pattern in a tray that is positionally registered to a dental arch of the patient; and repositioning the block of machinable material by the holder and forming a second planar surface of the surgical guide from the block of machinable material using the drilling tool to complete the surgical guide, wherein the second planar surface is parallel to the first planar surface, where the holder is configured to move the block of machinable material with respect to the drilling tool when forming the surgical guide only along each of orthogonal axes X, Y, and Z, and where the rotation axis is the X-axis, and where the rotation of the holder with respect to the drilling tool is only around the X axis.

2. The method of claim 1 wherein forming the first planar surface comprises milling the surface from the material using a lateral surface of the drilling tool.

3. The method of claim 2 wherein the first planar surface is oblique with respect to the orthogonal X, Y, and Z axes of a 4-axis milling machine.

4. The method of claim 1 wherein the tray is positionally registered to the dental arch of the patient using an impression forming material.

5. The method of claim 1 wherein the surgical guide is formed of metal.

6. The method of claim 1 wherein the surgical guide is formed of plastic.

7. The method of claim 1 further comprising obtaining information about the patient from a volume image and following an implant plan generated according to the obtained information.

8. The method of claim 1 further comprising mounting the surgical guide onto the tray by matching the hole and pin patterns.

9. The method of claim 8 further comprising drilling into a jaw bone of the patient through the drill guiding hole.

10. A method for forming a surgical guide for drilling of a dental patient, comprising:

rotating a metal material block about a rotation axis to a first angular position;

drilling a drill guiding hole through the metal material block using a drilling tool that has a drilling tool axis that is orthogonal to the rotation axis, wherein the drill guiding hole is centered about a drill guide axis that is substantially orthogonal to the rotation axis;

milling a first planar surface of the surgical guide from the metal material block, wherein the first planar surface is oblique to the drill guide axis, where milling the first planar surface comprises milling the surface from the material using a lateral surface of the drilling tool;

repositioning the metal material block to orient the first planar surface orthogonal to the drilling tool axis;

drilling a hole pattern having two or more positioning holes in the first planar surface using the drilling tool, wherein the hole pattern corresponds to a pin pattern in a tray that is positionally registered to a dental arch of the patient according to an impression obtained from the patient; and milling a second planar surface of the surgical guide to complete the surgical guide, wherein the second planar surface is parallel to the first planar surface.

11. The method of claim 10, where the milling is done using a 4-axis milling machine that comprises the drilling tool and a holder, where the material is mounted to the holder of the 4-axis milling machine, where the 4-axis milling machine is configured to move the material with respect to the drilling tool along each of orthogonal axes X, Y, and Z, and where the rotation axis is only the X-axis.

* * * * *